(12) United States Patent
Gallagher et al.

(10) Patent No.: US 7,439,391 B2
(45) Date of Patent: Oct. 21, 2008

(54) MULTI-STAGE GLYCOLIC ACID CRYSTALLIZATION

(75) Inventors: F. Glenn Gallagher, Wilmington, DE (US); Rod K. Hackman, Charleston, WV (US); Daniel Albert Green, Moylan, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/974,346

(22) Filed: Oct. 11, 2007

(65) Prior Publication Data

US 2008/0091047 A1    Apr. 17, 2008

Related U.S. Application Data

(60) Provisional application No. 60/851,517, filed on Oct. 12, 2006.

(51) Int. Cl.
    *C07C 51/43* (2006.01)
(52) U.S. Cl. .................................................. 562/580
(58) Field of Classification Search ................ None
    See application file for complete search history.

(56) References Cited

U.S. PATENT DOCUMENTS

| 2,260,738 | A |  | 10/1941 | Berhenke et al. |
| 2,285,886 | A |  | 6/1942 | Beck et al. |
| 5,853,639 | A |  | 12/1998 | Kawakami et al. |
| 6,001,439 | A |  | 12/1999 | Kawakami et al. |
| 6,159,416 | A |  | 12/2000 | Kawakami et al. |
| 6,245,437 | B1 |  | 6/2001 | Shiiki et al. |
| 7,002,039 | B2 |  | 2/2006 | van Krieken |
| 7,164,040 | B2 | * | 1/2007 | Kuroda et al. ............... 562/580 |
| 2004/0249206 | A1 |  | 12/2004 | van Krieken |
| 2005/0020853 | A1 |  | 1/2005 | Kuroda et al. |

FOREIGN PATENT DOCUMENTS

| WO | WO 92/05138 |   | 4/1992 |
| WO | WO 03/064366 | * | 9/2003 |
| WO | WO 2006/064611 A1 |  | 6/2006 |

* cited by examiner

*Primary Examiner*—James O. Wilson
*Assistant Examiner*—Yevegeny Valenrod

(57) ABSTRACT

The present invention relates to a high yield process to prepare high purity crystalline glycolic acid using a multi-loop crystallization process characterized by high liquid and/or solid recycle, said process suitable for large scale purification and producing high purity glycolic acid with low diglycolic acid content.

7 Claims, 2 Drawing Sheets

MULTI-STAGE GLYCOLIC ACID CRYSTALLIZATION

FIELD OF THE INVENTION

The present invention relates to a high yield process for producing high purity glycolic acid. Specifically, a multi-stage, high yield, crystallization process is used to produce high purity crystalline glycolic acid having very low impurities, especially diglycolic acid.

BACKGROUND OF THE INVENTION

Glycolic acid (HOCH2COOH; CAS Registry Number is 79-14-1) is the simplest member of the a-hydroxy acid family of carboxylic acids. Its properties make it ideal for a broad spectrum of consumer and industrial applications, including use in water well rehabilitation, the leather industry, the oil and gas industry, the laundry and textile industry, and as a component in personal care products. Glycolic acid also is a principal ingredient for cleaners in a variety of industries. Such cleaners include dairy and food processing equipment cleaners, household and institutional cleaners, metals processing cleaners (for metal pickling, copper brightening, etching, electroplating, electropolishing), and industrial cleaners (for transportation equipment, masonry, printed circuit boards, stainless steel boiler and process equipment, and cooling tower/heat exchangers).

Glycolic acid can also be used to produce a variety of polymeric materials, including thermoplastic resins comprising polyglycolic acid. Resins comprising polyglycolic acid have excellent gas barrier properties, and such thermoplastic resins comprising polyglycolic acid may be used to make packaging materials having excellent gas barrier properties (e.g., beverage containers, etc.). However, it is known that impurities within glycolic acid, such as diglycolic acid, may adversely impact the gas barrier properties of resins comprising polyglycolic acid. As such, there is a need to produce high purity glycolic acid.

A variety of industrial processes are used to produce glycolic acid, and each typically introduces impurities to the final glycolic acid product. Such processes include carbonylation of formaldehyde, oxidation of ethylene glycol, chloroacetic acid saponification, acid hydrolysis of glycolonitrile (with an optional glycolic acid ester intermediate), hydrolysis of methyl glycolate, and enzymatic hydrolysis of glycolonitrile. For example, glycolic acid obtained by carbonylation of formaldehyde in water, in the presence of an acid catalyst contains glycolic acid dimer or oligomers formed by ester-forming dehydrocondensation of glycolic acid, and diglycolic acid as major impurities in addition to residues of the catalysts. Patent application WO92/05138 (European Patent 0552255B1) describes that a 70% technical grade glycolic acid aqueous solution typically shows the following composition by weight percent: glycolic acid 62.4%, glycolic acid dimmer 8.8%, diglycolic acid 2.2%, methoxyacetic acid 2.2%, and formic acid 0.24%.

Purification of a hydroxycarboxylic acid can be difficult as heating often results in the formation of polycondensation products. As such, a purification process that involves significant heating, such as distillation, is difficult.

The use of crystallization to obtain a more purified form of glycolic acid has been reported in the art. Patent application WO2006/064611AI teaches a single stage, high yield crystallization process (yield of 95.5%). However, the process provides only a moderate purity improvement for diglycolic acid (88%), and does not describe a multi-stage process characterized by both high yield and high purity. Patent application WO2003/64366A1 (corresponding to US Patent application 2005/20853A1) teaches a single stage crystallization process capable of providing a highly purified glycolic acid product, but with relatively low recovery yield.

U.S. Pat. No. 7,002,039 claims a method for purification of an a-hydroxy acid by subjecting the starting material to at least two batch crystallization steps with "both crystallization steps preferably being carried out in one device." [column 4, lines 28-30]. This patent does not teach a continuous, multi-stage crystallization process having solid or liquid recycling, whereby high purity glycolic acid can be obtained in high yield.

Therefore a need still exists for a process that provides both high yield and high purity glycolic acid. The present invention provides such a process.

SUMMARY OF THE INVENTION

The present invention provides a high yield crystallization process capable of producing high purity crystalline glycolic acid. The high yield process comprises a plurality of crystallization loops characterized by high recycle (i.e., wherein the liquid or solid portions obtained from the crystallization process are recycled within and/or between crystallization loops) and a purge loss of less than 20 weight % of the total glycolic acid entering the system (i.e., high process yield) whereby high purity crystalline glycolic acid can be produced having very low levels of diglycolic acid impurity.

In one embodiment, a process for purification of glycolic acid based on liquid purge recycling comprises:
   a) providing a first aqueous feed stream comprising at least 60 weight % glycolic acid and at least 0.2 weight % of an undesirable impurity;
   b) isolating high purity crystalline glycolic acid using a crystallization process characterized by a product yield of at least 80% and a plurality of cascaded crystallization loops, said process comprising a first crystallization loop and a second crystallization loop;
   said first crystallization loop comprising:
      (i) a first crystallizer;
      (ii) a first evaporator;
      (iii) a first solid/liquid separator; and
      (iv) a first wash solution;
   wherein the first crystallization loop produces a first purge, a first washed solid crystalline product and a first washed mother liquor; wherein said first wash solution is an aqueous feed stream of glycolic acid; whereby the first purge from the first crystallization loop is less than 20% of the glycolic acid within said first aqueous feed stream; whereby said first washed solid crystalline product is dissolved with water forming a second aqueous feed stream comprising glycolic acid, said second aqueous feed stream fed into said second crystallization loop;
   said second crystallization loop comprising
      (v) a second crystallizer;
      (vi) a second evaporator;
      (vii) a second solid/liquid separator; and
      (viii) a second wash solution wherein said second wash solution is said second aqueous feed-stream whereby the second crystallization loop produces a second purge, a second washed mother liquor, and a second washed crystalline product, wherein the second purge is recycled back into said first crystallization loop; whereby high purity crystalline glycolic acid is produced.

The present invention further comprises the apparatus used in the process described above, as depicted in FIG. 1, which may include one or more additional loops. The present invention further comprises the high yield, high purity glycolic acid product produced from the process described above.

The present invention further comprises a multi-stage crystallization process based on a plurality of cascaded crystallization loops characterized by solid product recycle comprising:

a) providing a first aqueous feed stream comprising at least 60 weight % glycolic acid and at least 0.2 weight % of an undesirable impurity;

b) isolating high purity crystalline glycolic acid using a crystallization process characterized by a product yield of at least 80% and a plurality of cascaded crystallization loops, said process comprising a first crystallization loop and a second crystallization loop;

said first crystallization loop comprising:
(v) a first crystallizer;
(vi) a first evaporator;
(vii) a first solid/liquid separator; and
(viii) a first wash solution;

wherein said first wash solution is water and is distinct from said first aqueous feed stream and wherein the first crystallization loop produces a first washed crystalline product and a first washed mother liquor; whereby a portion of said first washed mother liquor is fed into a second crystallization loop;

said second crystallization loop comprising
(v) a second crystallizer;
(vi) a second evaporator;
(vii) a second solid/liquid separator; and
(viii) a second wash solution;

wherein the second wash solution is water and is distinct from said first washed mother liquor whereby the second crystallization loop produces a purge, a second washed mother liquor, and a second washed crystalline product, wherein the purge is less than 20% of the glycolic acid within said first aqueous feed stream and wherein the second washed crystalline product is recycled back into said first crystallization loop and wherein said first washed crystalline product is high purity crystalline glycolic acid.

The present invention further comprises the apparatus used in the process described above, as depicted in FIG. 2, which may include one or more additional loops. The present invention further comprises the high yield, high purity glycolic acid product produced from the multi-stage crystallization process described above.

The invention can be more fully understood from the Figures and the detailed description that together form this application.

The washed solid is dissolved with water (W2) upon leaving the first crystallization loop (from C) and enters the second crystallization loop in the second solid/liquid separator (G). The feed entering the second loop also acts as the wash liquid for the second loop. As in the first loop, the second crystallization loop includes: an optional second holding tank (H), a second evaporator (E) where water is removed (W3) to concentrate the glycolic acid solution, and a second crystallizer (F) wherein heat is removed (Q2) and the resulting solid/liquid mixture is separated using the second solid/liquid separator (G). The crystalline glycolic acid product is obtained from the second liquid/solid separator (G). A portion of the washed mother liquid obtained from the second solid/liquid separator is returned back to the first crystallization loop (second purge).

Figure 1:
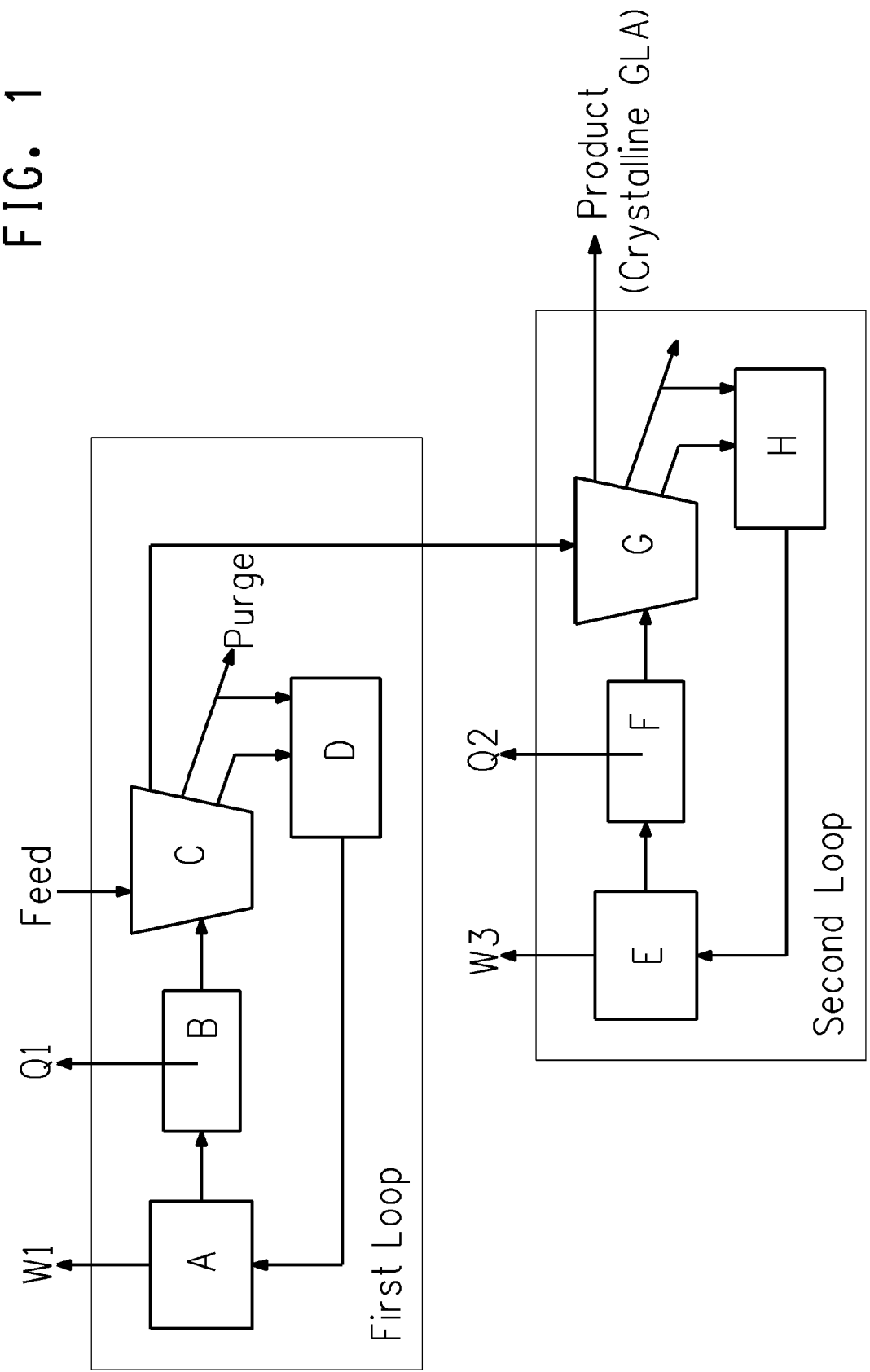
FIG. 1 shows the general design of a multi-loop, crystallization system using a high level of recycling of the liquid purge to produce high purity glycolic acid. Glycolic acid is used as the feed and the wash liquid for the first solid/liquid separator (C) where the resulting washed solid is dissolved in water (W2) and transferred to the second crystallization loop. The washed mother liquor obtained from the first solid/liquid separator (C) is subsequently recycled through the first crystallization loop via an optional holding tank (D) wherein additional water (W1) may be removed using a first evaporator (A) prior to reentering the first crystallizer (B) wherein heat is removed (Q1), and transferred to the solid/liquid separator (C).
Figure 2:
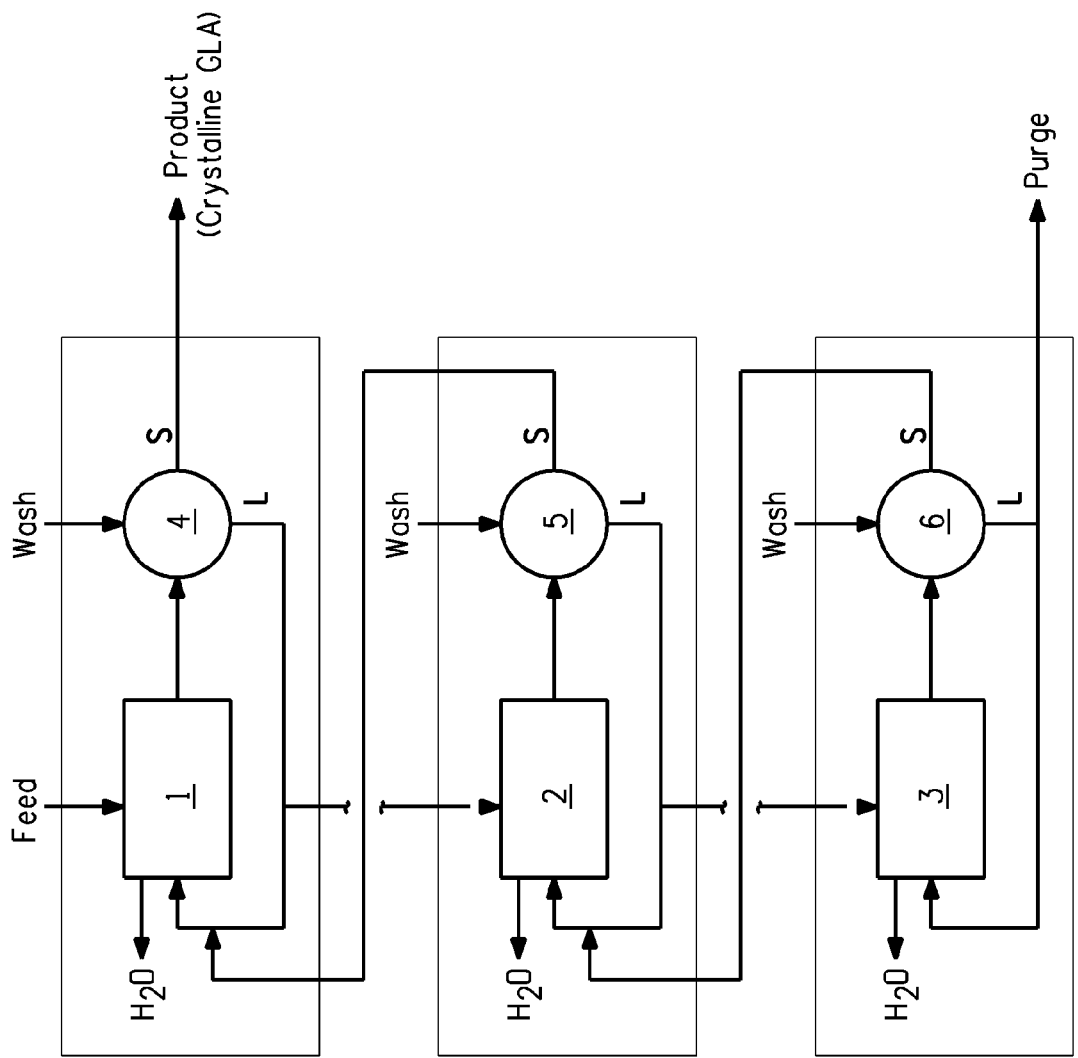

FIG. 2 depicts the general design of a cascading multi-module crystallization system to produce high purity glycolic acid. The solid recovery process illustrated in FIG. 2 begins with an aqueous glycolic acid feed stream (glycolic acid syrup) entering a first crystallization stage (1). In one embodiment, the concentration of glycolic acid in the feed may be adjusted prior to the first crystallization. The resulting aqueous solution comprising crystalline glycolic acid is transferred to a first solid/liquid separator (4) where the material is washed with water (wash liquid), forming a washed crystalline solid (S) and a washed mother liquor (L). As opposed to the process shown in FIG. 1, the wash liquid is water and not an aqueous feed comprising glycolic acid. The washed mother liquid (L) from (4) is recycled through the loop where a portion of the liquid is transferred to a second crystallization loop (2). In the second crystallization loop, the crystallization process described for the first crystallization loop is repeated and the aqueous solution comprising glycolic acid is transferred to the second solid/liquid separator (5) wherein the material is washed. The washed mother liquid (L) from (5) is recycled through the loop back to (2) wherein a portion of the liquid is transferred to a third crystallization loop (3). The washed solid (S) is cascaded back to the previous crystallization loop (1). The crystallization process above is repeated in further crystallization loops wherein the solid obtained from the subsequent crystallization loops is cascaded back into a previous crystallization loop whereby the high purity crystalline glycolic acid is accumulated and isolated from the first solid/liquid separator (4). A portion of the washed mother liquor from the final crystallization loop is purged at a rate to ensure at least 80 weight % recovery of the glycolic acid in the feed stream entering the process.

DETAILED DESCRIPTION OF THE INVENTION

The stated need has been solved by providing a high yield process to obtain high purity glycolic acid from an aqueous feed stream comprising glycolic acid having certain undesirable impurities (i.e., at least 0.2) weight % diglycolic acid). The continuous process of the present invention uses a plurality of crystallization steps with high recycle to produce high purity glycolic acid with high yield.

In this disclosure, a number of terms and abbreviations are used. The following definitions apply unless specifically stated otherwise.

As used herein, the term "weight percent" is abbreviated as "wt %" at various locations.

As used herein, the term "comprising" means the presence of the stated features, integers, steps, or components as referred to in the claims, but does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

As used herein, the term "glycolic acid" is synonymous with hydroxyacetic acid, hydroxyethanoic acid, and all other synonyms of CAS Registry Number 79-14-1.

As used herein, the term "diglycolic acid" is synonymous with 2,2'-oxybisacetic acid, 2,2'-oxydiacetic acid, and all other synonyms of CAS Registry Number 110-99-6.

As used herein, the terms "aqueous solution feed stream", "aqueous feed stream", "aqueous glycolic acid feed stream", "glycolic acid feed", and "feed" are used interchangeably to refer to an aqueous feed stream comprising glycolic acid. Typically, the feed stream comprises approximately about 60 weight % to about 90 weight % glycolic acid and at least about 0.2 weight % of an undesirable impurity, such as diglycolic acid. In one embodiment, the aqueous feed stream comprises 65 weight % to 85 weight % glycolic acid, wherein approximately 70 weight % is typical. In another embodiment, the concentration of glycolic acid in the aqueous feed stream is adjusted and/or concentrated prior to the first crystallization step. As shown in FIG. 1, the aqueous feed stream can be used as the wash for the first crystallization stage.

As used herein, the term "high yield process" refers to a process to produce high purity glycolic acid with at least 80% yield, preferably at least 90%, and most preferably at least 95% yield.

As used herein, the term "high purity glycolic acid" refers to the glycolic acid produced by the present process wherein at least 90%, preferably at least 95%, and most preferably at least 99% of the undesirable impurities in the aqueous feed stream have been removed.

As used herein, the term "undesirable impurity" refers to any impurity present within first aqueous feed stream comprising glycolic acid at a concentration that can adversely affect the gas barrier properties of a resin comprising polyglycolic acid. Technical grade glycolic acid (approximately 70 weight % glycolic acid) typically comprises at least 0.6 to 1 weight % diglycolic acid (6000 ppm to 10,000 ppm). It is known that substantial amounts of diglycolic acid within the technical grade glycolic acid can adversely impact the gas barrier properties of a resin comprising polyglycolic acid. In one aspect, the high purity glycolic acid produced by the present process comprises less than 2000 ppm diglycolic acid, preferably less than 1000 ppm diglycolic acid, more preferably less than 600 ppm diglycolic acid, even more preferably less than 400 diglycolic acid, more preferably less than 200 ppm diglycolic acid, and most preferably less than 100 ppm diglycolic acid.

As used herein, the terms "multi-stage crystallization", and "multi-loop crystallization" refer to the high yield process of the present invention comprising at least two crystallization loops as shown in FIGS. 1 and 2. In one embodiment as shown in FIG. 1, at least two crystallization loops are used wherein 1) the purge from the first loop is less than 20% glycolic acid and wherein the liquid purge from the second loop is recycled to the first loop and 2) wherein the feed stream to each loop is also used as the washing liquid. In another embodiment as shown in FIG. 2, at least two crystallization modules are used in a series wherein the solid isolated from each crystallization module is subsequently recycled back into a previous crystallization loop whereby a high purity glycolic acid solid is isolated from the first crystallization loop.

As used herein, the term "crystallization module" refers to a crystallization loop comprising at least one crystallizer, at least one evaporator/dehydrator, at least one solid/liquid separator, a washing liquid, and an optional, yet preferred, liquid accumulation tank. The crystallizer and evaporator/dehydrator can be combined into one unit.

In one aspect, any crystallization device (crystallizer) can be used including cooling crystallization devices, melting crystallization devices, evaporative crystallization devices, and/or adiabatic crystallization devices can be used. In a preferred embodiment, the crystallization device is a cooling crystallization device. In another aspect, a combination of crystallization devices can be used.

The glycolic acid within the aqueous glycolic acid feed stream can be produced by any number of well known industrial production processes including formaldehyde carbonylation, glycolonitrile hydrolysis (with or without intermediate esterification), ethylene glycol oxidation, chloroacetic acid saponification, and hydrolysis of glycolic acid esters (e.g., methyl glycolate), to name a few. Each process results in the production of impurities in varying amounts, including diglycolic acid. Non-enzymatic production methods typically produce technical grade glycolic acid having impurities that must be removed in order to make polyglycolic acid resins having the desired gas barrier properties. In a preferred aspect, the source of the glycolic acid feed is produce by the formaldehyde carbonylation method.

Typically, the aqueous glycolic acid concentration entering each crystallization stage is adjusted to a concentration generally ranging from about 50 weight % to about 90 weight %, preferably 60 weight % to 85 weight %, and most preferably 70 weight % to 85 weight %. Glycolic acid concentrations below 50 weight % typically result is a significant decrease in crystallization efficiency while concentrations in excess of 90 weight % are typically slurry having a viscosity that makes solid/liquid separation more difficult.

The concentration of glycolic acid can be adjusted by water removal or addition prior to crystallization. In one aspect, the water is removed using an evaporation device (e.g., an evaporator). Vacuum and/or heat can be applied to aid in the removal of water.

General crystallization methodology and equipment can be found in sections 18-35 through 18-54 of *Perry's Chemical Engineers' Handbook*, $7^{th}$ ed., Perry, Robert H., Green, Dow W., and Maloney, James O., editors; McGraw Hill Companies, Inc., New York, N.Y., 1997). Commercial designs for crystallization systems are illustrated in Perry's (see FIGS. 18-64 through 18-74).

The aqueous feed comprising glycolic acid is introduced into a crystallizer and cooled down to the crystallization point. The process optionally includes a pre-cooler prior to introducing the solution into the crystallizer to aid in the cooling process. The aqueous glycolic acid solution is typically cooled to a temperature of less than 50° C., preferably less than 20° C., and preferably to a temperature ranging from −20° C. to about 5° C. to induce crystallization.

The resulting glycolic acid solution containing crystalline glycolic acid is then subsequently transferred to a solid/liquid separator and washed, where separation can occur via any number of techniques including filtration, decantation, and/or centrifugation. The design of the solid/liquid separators is well known in the art (see Perry's, supra). In one aspect, the solid/liquid separator is a continuous centrifuge. A wash liquid (the aqueous glycolic acid feed stream in FIG. 1 or water in FIG. 2) is introduced into the solid/liquid separator to wash the crystalline glycolic acid free of the mother liquor. The washed mother liquor can be recycled through the crystallization loop where an evaporator is used to remove water (FIG. 1) or may be transferred to a subsequent crystallization loop for further processing (FIG. 2).

Each loop can include a means to evaporate/remove excess water from the liquid streams. Evaporators and means to evaporate water are well known in the art. The evaporator (a.k.a. the dehydration vessel) is typically used to remove excess water so that the concentration of glycolic acid entering the crystallizer is suitable for efficient crystallization. In one embodiment, the evaporator includes a means to heat the aqueous solution of glycolic acid. It is understood that excess temperature may result in the formation of undesirable glycolic acid-derived impurities. Generally, the aqueous glycolic acid solution is heated therein to a temperature typically ranging from about 50° C. to about 130° C. under normal or reduced pressure whereby the evaporated water is removed from the system. The evaporated water can be condensed using a total condenser and optionally collected.

One of skill in the art will recognize that the present process includes such elements as transfer lines, pumps, and similar conventional equipment. It is also understood that the present process design may optionally include pre-coolers, total condensers, stirring devices (e.g., internal to the evaporators, wash tanks, and holding tanks), and refrigeration devices suitable for cooling and inducing crystallization. In an optional embodiment, one or more of the crystallizers can be optionally seeded with glycolic acid crystals to enhance the crystallization process.

Two alternative embodiments of the process of the present invention are provided. In FIG. 1, a multi-loop crystallization process is shown wherein the incoming glycolic acid feed is used as the wash and the purge is recycled back into the first crystallization loop. In this process, a significant portion of the liquid (washed mother liquor) is recycled wherein the undesirable impurities accumulate in the liquid purge. The purge from the first loop is typically minimized so that less than 20% of the glycolic acid in the aqueous feed stream is purged while the purge from the second loop is recycled back to the first loop. In this way, a high purity crystalline glycolic acid product is formed from a high yield process.

FIG. 2 illustrates an alternative embodiment wherein the solids are recycled back into the first crystallization module. The resulting high yield process provides high purity glycolic acid product (solid) from the first crystallization loop. This alternative multi-loop crystallization process can be used to produce high purity glycolic acid from an aqueous feed comprising glycolic acid. Typically, the aqueous feed comprises approximately 60 to 90 weight % glycolic acid and at least 0.2 weight % of impurities, especially diglycolic acid. The alternative multi-loop can be used to purify glycolic acid regardless of the industrial process used to produce the aqueous glycolic acid feed stream. In a preferred aspect, the aqueous feed stream comprises approximately 70 weight % to 85 weight % glycolic acid produced by formaldehyde carbonylation as taught in Patent application WO 92/05138, European Patent 0552255B1.

A first embodiment of the present invention, depicted in FIG. 1, is a high yield, multi-loop crystallization system with liquid purge recycle. In one aspect, the multi-loop, crystallization process uses a first crystallization loop and at least one additional crystallization loop wherein the purge from the first crystallization loop is less than 20% (i.e., yield targeted to at least 80%) and the purge from each of the additional crystallization loops is recycled back into the first crystallization loop. In one aspect, the multi-stage crystallization process is a two-loop crystallization process as shown in FIG. 1.

FIG. 1 shows the general design of a multi-loop, crystallization system having high recycle, which is used to obtain purified glycolic acid with high yield from an aqueous solution of glycolic acid having various impurities such as diglycolic acid. Typically, the concentration of the glycolic acid in the aqueous feed ranges from approximately 60 weight % to about 90 weight %, wherein an aqueous feed of approximately 70 weight % to 85 weight % glycolic acid is typical.

The present process is based on a plurality of crystallization loops. The system shown in FIG. 1 depicts a multi-loop crystallization system composed of two recirculating crystallization loops. The basic crystallization loop consists of an evaporator (A) where water (W1) is removed from the recirculating liquid, a crystallizer (B) where the recirculating liquid is cooled (heat is removed, Q1) and a solid precipitates, a solid/liquid separation device (C) with the capability to wash the solid free of the mother liquor and the ability to separate the solid from the liquids (washed mother liquor), and an optional collection tank (D) to receive liquids from the solid/liquid device. The liquid moves through all four devices, i.e., evaporator, crystallizer, separator, and then the accumulation tank back to the evaporator.

In FIG. 1 the starting material (Feed) is also used as the wash fluid in the first separator (C). The product is the solid product from the separator. The liquid purge material comprises less than 20 weight % (preferably 4-7%) of the glycolic acid in the aqueous feed. All remaining liquids (washed mother liquor) are accumulated in the first tank (D). The liquid then enters the evaporator (A) where water (W1) is removed to achieve a desired final active concentration. The concentrate is cooled in the crystallizer where nominally 15 to 40% of the liquid precipitates. The resulting slurry is then fed back to the separator (C).

The product from the first loop (crystalline solid) is dissolved in water (W2) prior to being fed into the separator of the second crystallization loop (i.e., the aqueous solution comprising dissolved glycolic acid is used as the wash fluid for the second loop). The second loop includes a second evaporator (E) where water is removed (W3), a second crystallizer (F) where heat is removed (Q2), a second solid/liquid separator (G), and a second accumulation tank (H) for the liquid from the second solid/liquid separator (G). The final product (high purity, crystalline glycolic acid) emerges from the separator (G). The purge from the second loop is returned to the first crystallization loop, preferably into the first tank (D).

The purge is controlled so that 20% or less of the glycolic acid in the first aqueous feed stream is purged whereby the process has a yield of 80% or more. In one aspect, the purge is controlled so that no more than 10%, preferably less than 10%, more preferably about 4% to about 8% of the glycolic acid (on a weight basis) in the first aqueous feed stream is removed by the purge.

An alternative embodiment of the present invention, depicted in FIG. 2, is a high yield multi-stage crystallization system with cascaded product recovery by solid recycle. In this alternative embodiment, high yield, multi-stage crystallization process a cascade of at least two crystallization loops are used wherein the solid product obtained from each crystallization stage is returned back to at least one of the previous crystallization stages/loops. Once again, the multi-stage process uses at least two crystallization loops (3 are depicted in FIG. 2), wherein each stage generally includes: at least one crystallizer, a means to remove excess water (an evaporator/dehydration vessel), a wash liquid, and a means to separate the washed solid/liquids obtained from the crystallizer. The high purity crystalline glycolic acid is subsequently obtained from the first crystallization stage/loop.

The solid recovery process illustrated in FIG. 2 begins with an aqueous glycolic acid feed stream entering a first crystallization stage (1) comprising a crystallizer and evaporator. In one embodiment, the concentration of glycolic acid in the feed may be adjusted prior to the first crystallization. The concentration of the glycolic acid in the aqueous feed generally ranges from approximately 60 weight % to about 90 weight %, wherein a feed of approximately 70 weight % to 85 weight % glycolic acid is preferred. The feed entering the crystallizer is cooled, forming a mixture of crystalline glycolic acid (solid) and corresponding mother liquor. The resulting aqueous solution comprising crystalline glycolic acid is transferred to a first solid/liquid separator (4) where the material is washed with water (wash liquid), forming a washed crystalline solid (S) and a washed mother liquor (L). As opposed to the process shown in FIG. 1, the wash liquid is water and not an aqueous feed comprising glycolic acid. The washed solid (S) is the purified glycolic acid product. The washed mother liquid (L) from (4) is recycled through the first crystallization loop wherein an evaporator is used to remove water. A portion of the liquid is transferred to a second crystallization loop (2) preferably entering into the second crystallizer. The design of the second (and subsequent crystallization loops with the cascading series of loops) crystallization loop is very similar to the first loop. In the second crystallization loop, the crystallization process described above is repeated with solution comprising crystalline glycolic acid being transferred to a second solid/liquid separator (5) where the material is washed with water (wash liquid), forming a washed crystalline solid (S) and a washed mother liquor (L). The solid (S) is recycled from (5) to the prior crystallization loop (1) and the liquid (L) is fed back into crystallization loop (2). A portion of the liquid (L) from loop (2) is fed into crystallization loop (3) and the process repeated using the third solid/liquid separator (6). In further crystallization loops the process is repeated wherein the solid obtained from the subsequent crystallization loops is cascaded back into a previous crystallization loop and whereby the high purity crystalline glycolic acid is accumulated and isolated from the first solid/liquid separator (4). A portion of the washed mother liquor from the final crystallization loop is purged at a rate to ensure at least 80 weight % recovery of the glycolic acid in the feed stream entering the process.

The present invention further comprises the apparatus employed in the multi-loop crystallization process described above as shown in FIG. 1. The apparatus comprises 1) a first crystallization loop containing an evaporator (A), a crystallizer (B), a solid/liquid separator (C), and a collection tank (D), wherein said evaporator (A) has at least three outlets with a feed line from said collection tank (D) connected to one outlet, an exit line (W1) connected to the second outlet, and a discharge line into said crystallizer (B) connected to the third outlet, said crystallizer (B) has at least three outlets with a feed line from said evaporator (A) connected to one outlet, an exit line (Q1) connected to the second outlet, and a discharge line into said separator (C) connected to the third outlet, said separator (C) has at least four outlets with a feed line from said crystallizer (B) connected to one outlet, a second feed line connected to the second outlet, a discharge line connected to the third outlet, said discharge line having two branches wherein one branch leads into said collection tank (D) and the other branch into an exit purge, and an exit line connected to the fourth outlet leading to a second crystallization loop;

said collection tank (D) has at least two outlets with a feed line from said separator (C) connected to one outlet and a discharge line into said evaporator (A) connected to the second outlet;

2) a second crystallization loop containing an evaporator (E), a crystallizer (F), a solid/liquid separator (G), and a collection tank (H), wherein said evaporator (E) has at least three outlets with a feed line from said collection tank (H) connected to one outlet, an exit line connected to the second outlet, and a discharge line into said crystallizer (F) connected to the third outlet, said crystallizer (F) has at least three outlets with a feed line from said evaporator (E) connected to one outlet, an exit line (Q2) connected to the second outlet, and a discharge line into said separator (G) connected to the third outlet, said separator (G) has at least four outlets with a feed line from said crystallizer (F) connected to one outlet, a second feed line from the first crystallization loop connected to the second outlet, a discharge line connected to the third outlet, said discharge line having two branches wherein one branch leads into said collection tank (H) and the other branch leading to collection tank (D) in crystallization loop (1), and an exit line connected to the fourth outlet; and said collection tank (H) having at least two outlets with a feed line from said separator (G) connected to one outlet and a discharge line into said evaporator (E) connected to the second outlet.

The present invention further comprises the apparatus employed in the multi-stage crystallization process based on a plurality of cascaded crystallization loops as described above and shown in FIG. 2. The apparatus comprises 1) a first crystallization loop containing a crystallizer and an evaporator (1) and a solid/liquid separator (4) wherein said crystallizer (1) having at least four outlets wherein a feed line is connected to one outlet, a discharge line leading to said separator (4) is connected to the second outlet, a second discharge line is connected to the third outlet, and a recycle feed line from said separator (4) is connected to the fourth outlet, said recycle line having a branch leading to a second crystallization loop;

said separator (4) having at least four outlets wherein a feed line is connected to one outlet, a second feed line from said crystallizer/evaporator (1) is connected to the second outlet, a discharge line is connected to the third outlet, and a recycle line to said crystallizer/evaporator (1) is connected to the fourth outlet, said recycle line having a branch leading to a second crystallization loop;

2) a second crystallization loop containing a crystallizer and an evaporator (2) and a solid/liquid separator (5) wherein said crystallizer/evaporator (2) having at least four outlets wherein a feed line from the first crystallization loop is connected to one outlet, a discharge line leading to said separator (5) is connected to the second outlet, a second discharge line is connected to the third outlet, and a recycle feed line from said separator (5) is connected to the fourth outlet, said recycle line having a branch leading to an optional additional crystallization loop (3); and said separator (5) having at least four outlets wherein a feed line is connected to one outlet, a second feed line from said crystallizer/evaporator (2) is connected to the second outlet, a recycle line is connected to the third outlet leading to the first crystallization loop, and a second recycle line to said crystallizer/evaporator (2) is connected to the fourth outlet, said second recycle line having a branch leading to an optional additional crystallization loop (3). In the final crystallization loop, this final branched recycle line exits to a purge instead of an additional crystallization loop.

Applicants specifically incorporate by reference the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

Example 1

This example uses equipment/system illustrated in FIG. 1. The system is composed of two recirculating loops of liquid. The basic loop consist of an evaporator where water is removed from the recirculating liquid, a crystallizer where the recirculating liquid is cooled and a solid precipitates, a solid/liquid separation device with the capability to wash the isolated solid and the ability to separately remove the solid from the liquids, and a collection tank to receive liquids from the solid/liquid device. The liquid moves through all four devices, i.e., evaporator, crystallizer, separator, and then the accumulation tank back to the evaporator.

In this example the starting material is used as the wash fluid in the first separator. The product is the solid product from the separator. The purge material is a portion of the liquid from the initial separation. All remaining liquids are accumulated in the first tank. The liquid then enters the evaporator where water is removed to achieve a desired final active concentration. The concentrate is cooled in the crystallizer where nominally 35% of the liquid precipitates. The resulting slurry is then fed to the separator.

The product from the first loop is diluted with water and used as the wash fluid for the second loop. The final product emerges from the separator. The purge from the second loop is returned to the tank in the first loop.

The calculated composition of the material at various locations (aqueous feed, purge, and crystalline product) within the double loop configuration of FIG. 1 based on mass flow calculations (mass/unit time) varies as the relative mass flow of product to purge varies and is provided in Tables 1, 2, and 3.

Example 2

This example uses the equipment/system illustrated in FIG. 2. The system is composed of a series of crystallizers (crystallizer modules) to systematically isolate solid product from an increasingly impure liquid. The solid from each stage is returned to the previous stage. The final product is purged from the initial crystallizer. The concentrated impurity (molasses) is purged from the final crystallizer.

The calculated composition of the material at various locations within the cascaded crystallization with solid recycle configuration as shown in FIG. 2 varies as the relative mass flow of product to purge and is provided in Tables 1, 2, and 3.

TABLE 1

Mass flow summary (mass per unit time) at various locations with high purge rate.

| Stream | Feed | Purge | Product |
|---|---|---|---|
| Total | 600 | 95 | 366.0 |
| GA[a] | 420 | 62 | 358.3 |
| DGA[b] | 4.8 | 4.3 | 0.5 |
| Other | 175 | 29 | 7.321 |
| GA | 70% | 65% | 98% |
| DGA | 1% | 4.6% | 0.128% |
| Other | 29% | 30% | 2% |

GA Recovery Yield = 85.3%
DGA Removal = 90%
[a]GA is glycolic acid
[b]DGA is diglycolic acid

TABLE 2

Mass flow summary (mass per unit time) at various locations with moderate purge rate.

| Stream | Feed | Purge | Product |
|---|---|---|---|
| Total | 600 | 60 | 386.0 |
| GA[a] | 420 | 42 | 378.0 |
| DGA[b] | 4.8 | 4.5 | 0.3 |
| Other | 175 | 14 | 7.7 |
| GA | 70% | 70% | 98% |
| DGA | 1% | 7.5% | 0.078% |
| Other | 29% | 23% | 2% |

GA Recovery Yield = 90.0%
DGA Removal = 94%
[a]GA is glycolic acid
[b]DGA is diglycolic acid

TABLE 3

Mass flow summary (mass per unit time) at various locations with low purge rate.

| Stream | Feed | Purge | Product |
|---|---|---|---|
| Total | 600 | 40 | 400.2 |
| GA[a] | 420 | 28 | 392.0 |
| DGA[b] | 4.8 | 4.6 | 0.2 |
| Other | 175 | 7 | 8.0 |
| GA | 70% | 70% | 98% |
| DGA | 1% | 11.5% | 0.050% |
| Other | 29% | 19% | 2% |

GA Recovery Yield = 93.3%
DGA Removal = 96%
[a]GA is glycolic acid
[b]DGA is diglycolic acid

What is claimed is:

1. A process for the purification of glycolic acid comprising:
   (a) providing a first aqueous feed stream comprising at least 60 weight % glycolic acid and at least 0.2 weight % of an undesirable impurity;
   (b) isolating high purity crystalline glycolic acid using a crystallization process characterized by a product yield of at least 80% and a plurality of cascaded crystallization loops, said process comprising a first crystallization loop and a second crystallization loop; said first crystallization loop comprising:
      (i) a first crystallizer;
      (ii) a first evaporator;
      (iii) a first solid/liquid separator; and
      (iv) a first wash solution;
   wherein the first crystallization loop produces a first purge, a first washed solid crystalline product and a first washed mother liquor; wherein said first wash liquid is an aqueous feed stream of glycolic acid; whereby the first purge from the first crystallization loop is less than 20% of the glycolic acid within said first aqueous feed stream; whereby said first washed solid crystalline product is dissolved with water forming a second aqueous feed stream comprising glycolic acid, said second aqueous feed stream fed into said second crystallization loop; said second crystallization loop comprising
      (v) a second crystallizer;
      (vi) a second evaporator;
      (vii) a second solid/liquid separator; and
      (viii) a second wash solution;
   wherein said second wash liquid is said second aqueous feed stream whereby the second crystallization loop produces a second purge, a second washed mother liquor, and a second washed crystalline product, wherein the second purge is recycled back into said first crystallization loop; whereby high purity crystalline glycolic acid is produced.

2. The process of claim 1, wherein said second washed crystalline product is said high purity crystalline glycolic acid.

3. The process of claim 1, wherein said first crystallization loop further comprises a first holding tank located between said first solid/liquid separator and said first evaporator wherein said second purge is recycled back into said first holding tank.

4. The process of claim 1 wherein said second crystallization loop further comprises a second holding tank located between said second solid/liquid separators and said second evaporator.

5. The process of claim 2, wherein said first purge is 4 weight % to 7 weight % of the total glycolic acid within said aqueous feed stream.

6. The process of claim 1, wherein said aqueous feed stream comprises 70 weight % to 85 weight % glycolic acid.

7. The process of claim 1, wherein said process comprises more than two cascaded crystallization loops wherein the total purge of said process is less than 10% of the glycolic acid with said aqueous feed stream and wherein the purge from said cascaded crystallization loops downstream of said first crystallization loop is recycled back into at least one previous crystallization loop.

* * * * *